United States Patent
Mehta et al.

(10) Patent No.: US 11,147,810 B2
(45) Date of Patent: Oct. 19, 2021

(54) PHARMACEUTICAL COMPOSITION OF ORAL SUSPENSION OF ANTI-NEOPLASTIC ALKYLATING AGENTS

(71) Applicant: FTF Pharma Private Limited, Ahmedabad (IN)

(72) Inventors: Sandip Mehta, Ahmedabad (IN); Manish Umrethia, Ahmedabad (IN); Henil Patel, Ahmedabad (IN); Jayanta Kumar Mandal, Ahmedabad (IN)

(73) Assignee: FTF PHARMA PRIVATE LIMITED, Ahmedabad (IN)

( * ) Notice: Subject to any disclaimer, the term of this patent is extended or adjusted under 35 U.S.C. 154(b) by 0 days.

(21) Appl. No.: 16/494,011

(22) PCT Filed: Mar. 12, 2018

(86) PCT No.: PCT/IB2018/051596
§ 371 (c)(1),
(2) Date: Sep. 13, 2019

(87) PCT Pub. No.: WO2018/167627
PCT Pub. Date: Sep. 20, 2018

(65) Prior Publication Data
US 2020/0069678 A1    Mar. 5, 2020

(30) Foreign Application Priority Data
Mar. 13, 2017 (IN) .............................. 201721008647

(51) Int. Cl.

| A61K 31/495 | (2006.01) |
|---|---|
| A61P 35/00 | (2006.01) |
| A61K 9/00 | (2006.01) |
| A61K 47/02 | (2006.01) |
| A61K 47/10 | (2017.01) |
| A61K 47/14 | (2017.01) |

(52) U.S. Cl.
CPC .......... *A61K 31/495* (2013.01); *A61K 9/0053* (2013.01); *A61K 47/02* (2013.01); *A61K 47/10* (2013.01); *A61K 47/14* (2013.01); *A61P 35/00* (2018.01)

(58) Field of Classification Search
CPC .... A61K 31/495; A61K 9/0053; A61K 47/02; A61K 47/10; A61K 47/14; A61P 35/00
See application file for complete search history.

(56) References Cited

U.S. PATENT DOCUMENTS

| 6,346,524 B1 * | 2/2002 | Ragab .................. A61K 31/395 514/183 |
|---|---|---|
| 2016/0199302 A1 * | 7/2016 | Lim ...................... A61K 9/1694 514/393 |

FOREIGN PATENT DOCUMENTS

| CN | 101309686 A | 11/2008 |
|---|---|---|
| CN | 101869551 A | 10/2010 |
| EP | 2939662 A1 | 11/2015 |

OTHER PUBLICATIONS

Trissei, "Temozolomide Stability in Extemporaneously Compounded Oral Suspensions", International Journal of Pharmaceutical Compounding, 10(5), Sep./Oct. 2006, pp. 396-399.*
International Search Report and Written Opinion issued in PCT Application PCT/IB2018/051596, dated Jan. 6, 2018.
Allen Jr, L.V., "Temololomide 10-mg/mL Oral Liquid", International Journal of Pharmaceutical Compounding, vol. 4, No. 11, p. 336.
Allen Jr, L.V., "Busulfan oral suspension", U.S. Pharmacist, Jobson Pub.vol 15, No. 11, Feb. 1, 1990, pp. 94-95.
Kennedy, R. et al., "Stability of cyclophosphamide in extemporaneous oral suspensions", The Annals of Pharmacotherapy, 1542-6270, vol. 44, No. 2, Feb. 1, 2010, pp. 295-301.

* cited by examiner

*Primary Examiner* — Sahar Javanmard
(74) *Attorney, Agent, or Firm* — Benesch, Friedlander, Coplan & Aronoff LLP

(57) ABSTRACT

The present invention provides pharmaceutical composition of antineoplastic alkylating agent in oral suspension dosage form. The oral suspension composition comprises of alkylating agent with other pharmaceutical excipients such as vehicle, preservative, antioxidant, suspending agent, surfactant, sweetener and flavouring agent. The present invention is an oral suspension having improved stability and palatability. The present invention also provides oral solution with flavor that has masked bitter taste of the drug. Further, the present invention also provides a process for preparation thereof.

4 Claims, No Drawings

PHARMACEUTICAL COMPOSITION OF ORAL SUSPENSION OF ANTI-NEOPLASTIC ALKYLATING AGENTS

FIELD OF THE INVENTION

The present invention relates to the oral liquid pharmaceutical composition of antineoplastic alkylating agents for treatment of certain cancers. More particularly, the present invention relates to oral suspension composition comprises of alkylating agent with improved stability and palatability.

BACKGROUND OF THE INVENTION

Cancer is a worldwide problem. Millions of people die in the world every year due to cancer. So, finding new compositions of antineoplastic drugs for the treatment of cancer is a crucial need. The treatment of cancer can be of three general categories: chemotherapy, radiation therapy and surgery. Chemotherapeutic drug work by interfering with cell cycle progression or by generating breaks in DNA.

Alkylating agents are chemotherapy drugs that bind to DNA and prevent proper DNA replication. So, alkylating agents are used as part of chemotherapy in different types of cancers. They have chemical groups that can form permanent covalent bonds with nucleophilic substances in the DNA. More specifically, an alkylating agent used in cancer treatment that attaches an alkyl group to DNA. The alkyl group is attached to the guanine base of DNA, at the number 7 nitrogen atom of the purine ring. This alkylation damages the DNA that leads to death of tumor cells. These drugs work in all phases of the cell cycle and are used to treat many different types of cancers.

Important antineoplastic alkylating agents include altretamine, busulfan, carboplatin, carmustine, chlorambucil, cisplatin, cyclophosphamide, dacarbazine, lomustine, melphalan, oxalaplatin, temozolomide and thiotepa. Currently available all of the alkylating agents used for chemotherapy are generally given orally in solid dosage form or intravenous injections.

EP2939662 discloses pharmaceutical composition of an alkylating agent in dry granules form with tartaric acid as a pH stabilizer and a method of preparing the same.

U.S. Pat. No. 6,346,524 relates to a method for treating cancer by administering an antineoplastic agent in oral solid dosage form preferably capsule.

CN101869551 discloses Temozolomide lyophilized composition for injection.

CN101309686 discloses pharmaceutical composition of Temozolomide and a pharmaceutically acceptable carrier in unit dosage form of capsule.

But, oral liquid dosage is more patient compliance as solid dosage form is difficult to swallow for few patients. In case of Temozolomide solid dosage forms, the dose to be taken is based on body surface area. For certain body surface area category of patients, it requires 4-6 units to be taken orally to get desired dose, which is a major drawback of solid dosage forms for those patients and specially, if they have difficulty to swallow solid dosage forms.

Temozolomide is approved for brain cancer. It is not possible for those patients to take solid dosage forms orally up to 72 hr from brain surgery and they have to rely on injectable Temozolomide.

Injection dosage is also not convenient when the drug is needed to administer more than once per day. Administration of injectable products either require hospitalization or medical staff.

Further, alkylating agents have strong bitterness and astringency that results a bitter taste and a feeling of numbness in the mouth.

To overcome such issues, there is a need for development of oral liquid dosage form that is stable, patient compliance having flavor that masks bitter taste of therapeutic agents as well as can be administered by tube directly in to gastrointestinal system within 72 hr of surgery.

The present invention is directed to flavored liquid suspension composition of antineoplastic alkylating agent that has masked bitter taste of active ingredient.

Further, currently inventive formulation is exhibiting improved stability and palatability.

OBJECTS OF THE INVENTION

The main object of the present invention is to provide oral pharmaceutical suspension of antineoplastic alkylating agent with improved stability and palatability.

Another object of the present invention is to provide oral suspension of antineoplastic alkylating agent with flavor that has masked bitter taste of the active ingredient.

Another object of the present invention is to provide oral suspension of alkylating agent that exhibits similar bioavailability to current solid dosage form available in the market.

Another object of present invention is to provide oral suspension having dose flexibility for patients who need special doses of the drug and have difficulties in swallowing oral solid dosage forms.

Still another object of the present invention is to provide a convenient process for preparation of oral pharmaceutical suspension of alkylating agent.

SUMMARY OF THE INVENTION

The present invention relates to an oral pharmaceutical suspension of an antineoplastic alkylating agent with improved stability and palatability. The present invention provides oral pharmaceutical suspension of an alkylating agent with flavor that has masked unpleasant taste of the drug.

Another aspect of the present invention relates to oral suspension of an antineoplastic alkylating agent that comprises an active ingredient with an antioxidant and other pharmaceutically acceptable excipients such as vehicle, suspending agent, preservative, sweetener, surfactant and flavouring agent. The present invention also provides a process for preparation thereof.

DETAILED DESCRIPTION OF THE INVENTION

Alkylating agents are used in cancer treatment. The alkyl group of alkylating agent is attached to the guanine base of DNA, at the number 7 nitrogen or O-6 positions. This alkylation damages the DNA that leads to death of tumor cells.

The present invention relates to an oral pharmaceutical suspension of antineoplastic alkylating agent with improved stability, palatability and higher rate of bioavailability.

The present invention comprises an active ingredient with other pharmaceutically acceptable excipients such as vehicle, preservative, suspending agent, antioxidant, sweetener, surfactant and flavouring agent. The present invention also provides a process for preparation thereof.

In the present invention, the active pharmaceutical ingredient for oral suspension dosage form is selected but not limited from alkylating agents such as altretamine, busulfan, carboplatin, carmustine, chlorambucil, cisplatin, cyclophosphamide, dacarbazine, lomustine, melphalan, oxalaplatin, temozolomide and thiotepa.

In an embodiment of the present invention, the alkylating agent is Temozolomide.

Temozolomide is having an empirical formula of $C_6H_6N_6O_2$ and a molecular weight of 194.2, chemically 3-methyl-8-carbamoyl-imidazo[5,1-d]-1,2,3,5-tetrazin-4 (3H)-one, and having the chemical structure as follows:

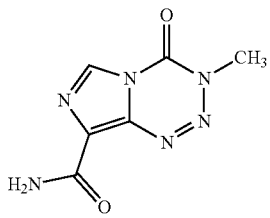

Temozolomide is known for its alkylating antitumor effects. Temozolomide is approved as a second-line treatment for astrocytoma and a first-line treatment for glioblastoma multiforme. This compound works by alkylating DNA, typically through addition of a methyl group to guanine in genomic DNA that leads to arrest at the $G_2$/M cell cycle and triggers the death of tumor cells.

Temozolomide is available in the market under the brand names Temodar or Temodal in hard capsule dosage form containing 5 mg, 20 mg, 100 mg or 250 mg Temozolomide. In capsule formulation of Temozolomide, active ingredient is contained at a high dosage per capsule, so it is difficult to achieve the full and uniform content. Further, it might be difficult to swallow solid dosage of the drug for all patients.

One aspect of the present invention relates to oral pharmaceutical composition in suspension dosage comprises Temozolomide as active ingredient and pharmaceutically acceptable excipients. Pharmaceutically acceptable excipients may include vehicle, suspending agent, preservative, antioxidant, sweetener, surfactant and flavouring agent. The present invention also provides a process for preparation of the same.

Alkylating agents may undergo hydrolysis in presence of water and therefore, it is a challenge to develop stable oral liquid dosage form for alkylating agents.

Temozolomide is a prodrug and is rapidly hydrolyzed into 5-(3-methyltriazen-1-yl imidazole-4-carboxamide (MTIC) at neutral and alkaline pH values. This molecule further gets hydrolyzed at acidic pH (<5), hence it is available as a lyophilized powder for injection in market.

Vehicles used in the present pharmaceutical composition are mainly liquid which carry active ingredient and other excipients in dissolved or dispersed state.

Pharmaceutical vehicles can be classified as aqueous vehicles and oily vehicles. Aqueous vehicles include water, hydro-alcoholic, polyhydric alcohols and buffers. Oily vehicles include vegetable oils, mineral oils, organic oily bases or emulsified bases. In the present invention, preferably medium chain triglyceride is used as vehicle as it exhibits excellent stabilization capability for alkylating agents which are sensitive to hydrolysis.

As Temozolomide is unstable in presence of water, one of the aspects of this invention is to develop stable liquid dosage formulation of Temozolomide.

Preservatives are included in pharmaceutical dosage form and prevent the growth of microorganisms during the product manufacturing and shelf life. Preservatives can be selected from but not limited to propyleneglycol, benzoic acid, potassium sorbate, sodium benzoate, chlorobutanol, ethanol. In the present invention, preferably ethanol is used as preservative.

Suspending agents help active pharmaceutical ingredients stay suspended in the formulation and prevent caking at the bottom of the container. A well-formulated suspension can be easily re-suspended by the use of moderate agitation or shaking. The main suspending agent employed in oral preparations can be selected from but not limited to carrageenan, cellulose ether, xanthan gum, sodium alginate, microcrystalline cellulose. In the present invention, preferably colloidal silicone dioxide is used as suspending agent.

Antioxidants can reduce a drug oxidation. Antioxidants can also act as chain terminators, reacting with free radicals in liquid to stop the free-radical propagation cycle. Oxidation may lead to products with an unpleasant odour, taste, appearance, precipitation, discoloration or even a slight loss of activity. The main antioxidants employed in oral preparations can be selected from but not limited to α-Tocopherol acetate, ascorbic acid, butylatedhydroxytoluene (BHT), sodium bisulfite.

In the present invention, preferably butylatedhydroxytoluene (BHT) is used as antioxidant.

Surfactants decrease the interfacial tension between drug particles and liquid thus liquid is penetrated in the pores of drug particle displacing air from them and thus ensures wetting. The main surfactants employed in oral preparations can be selected from but not limited to polysorbate 80, poloxamer, alkyl sulfates. In the present invention, preferably labrasol is used as surfactant.

Sweetening agents are added in liquid formulations that impart sweetness and improve patient compliance through taste masking. The main sweetening agents employed in oral preparations can be selected from but not limited to sucrose, liquid glucose, glycerol, sorbitol, saccharin sodium and aspartame. In the present invention, preferably sucralose is used as sweetener.

Flavoring agents are added to increase patient acceptance of the drug by masking the specific taste sensations. Flavoring agent can be selected but not limited to essential oils including peppermint oil, orange oil, and lemon oil or can be selected from fruit flavors. In the present invention, preferably peppermint flavor is used.

Below table represents the composition of the present invention.

| Sr No | Name of Ingredients | Formula % w/w |
|---|---|---|
| 1 | API | 5-50% |
| 2 | Preservative | 1-10% |
| 3 | Antioxidant | 0.001-2% |
| 4 | Suspending agent | 0.1-20% |
| 5 | Surfactant | 0.01-10% |
| 6 | Sweetener | 0.001-10% |
| 7 | Flavouring agent | 0.001-2% |
| 8 | Vehicle | Q.S. |

The oral pharmaceutical suspension of above composition is prepared by following steps irrespective to order of addition, but not limited to:

A) Add suspending agent, surfactant, anti-oxidant, preservative, sweetener, flavouring agent one by one till it dissolve or disperse;

B) Add API and mix till it dissolve or disperse;
C) Make volume up to desired batch size.

EXAMPLES

The present invention can be described by way of examples only. They are not to be construed to limit the invention in any manner whatsoever. The following examples are intended to illustrate the various aspects of the invention, though without aiming to limit it.

Below table represents the composition of 150 mg/5 ml Temozolomide and excipients with its range are shown below:

Example: Oral Suspension of Temozolomide (150 mg/5 ml)

| Sr No | Name of Ingredients | Formula mg/ml |
|---|---|---|
| 1 | Temozolomide | 30.0 |
| 2 | Ethanol (5% v/v) | 40 |
| 3 | BHT (Butoxylatedhydroxytoluene) | 0.15 |
| 4 | Sucralose | 1 |
| 5 | Colloidal silicone dioxide | 10 |
| 6 | Peppermint flavor | Q.S. |
| 7 | Labrasol | 30 |
| 8 | Medium chain triglyceride miglyol (kollisolv 70) | Q.S. |

The oral pharmaceutical suspension of above composition is prepared by following steps but not limited to:
A) Add suspending agent, surfactant, anti-oxidant, preservative, sweetener, flavouring agent one by one till it dissolve or disperse;
B) Add API and mix till it dissolve or disperse;
C) Make volume up to desired batch size.

We claim:
1. A pharmaceutical composition of oral liquid suspension of antineoplastic alkylating agent comprising:
   5-50 w/w % temozolomide;
   a stabilizer consisting of a medium chain triglyceride and devoid of acidic stabilizer;
   1-10 w/w % preservative that is one of: propylene glycol, benzoic acid, potassium sorbate, sodium benzoate, chlorobutanol, or ethanol;
   0.001-2 w/w % antioxidant that is one of: α-Tocopherol acetate, ascorbic acid, butylated hydroxytoluene (BHT), or sodium bisulfite;
   0.1-20 w/w % suspending agent that is one of carrageenan, cellulose ether, xanthan gum, sodium alginate, microcrystalline cellulose or colloidal silicone dioxide;
   0.01-10 w/w % surfactant this is one of: polysorbate 80, poloxamer, alkyl sulfates, or labrasol;
   0.001-10 w/w % sweetener that is one of: sucrose, liquid glucose, glycerol, sorbitol, saccharin sodium, aspartame, or sucralose;
   and pharmaceutically acceptable excipients with improved stability.
2. The pharmaceutical composition of claim 1, wherein the composition is with flavor that has masked bitter taste of the drug.
3. A process for preparation of the pharmaceutical composition of claim 1 comprising following steps:
   (a) adding temozolomide to the stabilizer and mixing until dissolved or dispersed;
   (b) adding the suspending agent, surfactant, anti-oxidant, preservative, sweetener, flavouring agent and mixing until dissolved or dispersed;
   (c) adjusting volume to desired amount.
4. A pharmaceutical composition of oral liquid suspension of antineoplastic alkylating agent comprising:
   30 mg temozolomide;
   a stabilizer consisting of a medium chain triglyceride and devoid of acidic stabilizer;
   40 mg ethanol;
   0.15 mg butylated hydroxytoluene (BHT);
   1 mg sucralose;
   10 mg colloidal silicone dioxide;
   30 mg labrasol;
   a flavouring agent that is an essential oil including peppermint oil, orange oil, lemon oil, or fruit flavors in a quantity sufficient that has masked bitter taste of the drug; and pharmaceutically acceptable excipients with improved stability.

* * * * *